(12) United States Patent
Focia et al.

(10) Patent No.: US 9,207,192 B1
(45) Date of Patent: Dec. 8, 2015

(54) MONITORING DIELECTRIC FILL IN A CASED PIPELINE

(71) Applicant: WaveTrue, Inc., New York, NY (US)

(72) Inventors: Ronald J. Focia, Edgewood, NM (US); Charles A. Frost, Albuquerque, NM (US)

(73) Assignee: WaveTrue, Inc., New York, NY (US)

( * ) Notice: Subject to any disclaimer, the term of this patent is extended or adjusted under 35 U.S.C. 154(b) by 216 days.

(21) Appl. No.: 13/904,998

(22) Filed: May 29, 2013

Related U.S. Application Data

(63) Continuation of application No. 12/728,143, filed on Mar. 19, 2010, now abandoned.

(60) Provisional application No. 61/161,714, filed on Mar. 19, 2009.

(51) Int. Cl.
| | |
|---|---|
| *G01R 31/00* | (2006.01) |
| *G01N 23/00* | (2006.01) |
| *G01R 31/12* | (2006.01) |
| *G01R 31/11* | (2006.01) |
| *G01R 31/02* | (2006.01) |
| *G01N 29/30* | (2006.01) |
| *G01M 3/18* | (2006.01) |

(52) U.S. Cl.
CPC .............. *G01N 23/00* (2013.01); *G01R 31/021* (2013.01); *G01R 31/11* (2013.01); *G01R 31/12* (2013.01); *G01M 3/18* (2013.01); *G01N 29/30* (2013.01)

(58) Field of Classification Search
CPC ....................................................... G01N 23/00
USPC ............................................................ 702/58
See application file for complete search history.

(56) References Cited

U.S. PATENT DOCUMENTS

| 2,698,923 A | 1/1955 | Edson |
| 2,849,683 A | 8/1958 | Miller |

(Continued)

FOREIGN PATENT DOCUMENTS

| DE | 3016223 | 11/1980 |
| EP | 399583 | 11/1990 |

(Continued)

OTHER PUBLICATIONS

Schmitz et al., German magazine "Nachrichten Elektronik + Telematik", vol. 37, No. 3, Mar. 1983, 7 pages, Heidelberg, Germany.

(Continued)

*Primary Examiner* — Paul D Lee
(74) *Attorney, Agent, or Firm* — Michael R. Schacht; Schacht Law Office, Inc.

(57) ABSTRACT

An inspection system employs a cased pipeline structure, a pulse generator system, a data acquisition system, and a processing system. The cased pipeline structure comprises a casing pipe structure, a carrier pipe structure arranged within the casing pipe structure to define an annular space, and fill material arranged within the annular space. The pulse generator system is configured to apply an electromagnetic signal to the cased pipeline structure. The data acquisition system is configured to detect electromagnetic signals propagating along the cased pipeline structure. The processing system analyzes electromagnetic signals detected by the data acquisition system for signal characteristics indicative of an anomaly in the cased pipeline structure.

20 Claims, 6 Drawing Sheets

(56) References Cited

U.S. PATENT DOCUMENTS

| | | | |
|---|---|---|---|
| 2,887,652 A | 5/1959 | Bendayan et al. | |
| 3,079,552 A | 2/1963 | Walker | |
| 3,600,674 A | 8/1971 | Roberts et al. | |
| 3,909,712 A | 9/1975 | Rietz et al. | |
| 4,178,576 A | 12/1979 | Schmidt, Jr. et al. | |
| 4,291,204 A | 9/1981 | Crick | |
| 4,523,473 A | 6/1985 | Chamuel | |
| 4,932,810 A | 6/1990 | Austin | |
| 4,970,467 A | 11/1990 | Burnett | |
| 4,982,198 A | 1/1991 | Shafai et al. | |
| 5,087,873 A | 2/1992 | Murphy et al. | |
| 5,122,773 A | 6/1992 | Chahbazian | |
| 5,189,374 A | 2/1993 | Burnett | |
| 5,243,294 A | 9/1993 | Burnett | |
| 5,270,661 A | 12/1993 | Burnett | |
| 5,389,216 A | 2/1995 | Balkanli | |
| 5,404,104 A | 4/1995 | Rivola et al. | |
| 5,719,503 A | 2/1998 | Burnett | |
| 5,747,998 A | 5/1998 | Fowler et al. | |
| 5,793,293 A | 8/1998 | Melamud et al. | |
| 5,828,219 A | 10/1998 | Hanlon et al. | |
| 5,828,220 A | 10/1998 | Carney et al. | |
| 5,854,557 A | 12/1998 | Tiefnig | |
| 5,859,537 A | 1/1999 | Davis et al. | |
| 5,864,229 A | 1/1999 | Lund | |
| 5,905,194 A | 5/1999 | Strong | |
| 5,933,012 A | 8/1999 | Bengtsson et al. | |
| 5,942,687 A | 8/1999 | Simmonds et al. | |
| 6,005,396 A | 12/1999 | Suyama et al. | |
| 6,020,733 A | 2/2000 | Bradley | |
| 6,051,977 A | 4/2000 | Masuda et al. | |
| 6,064,903 A * | 5/2000 | Riechers et al. | 600/407 |
| 6,065,348 A | 5/2000 | Burnett | |
| 6,072,316 A | 6/2000 | Burnett | |
| 6,078,280 A | 6/2000 | Perdue et al. | |
| 6,137,449 A | 10/2000 | Kildal | |
| 6,157,183 A | 12/2000 | Bradley | |
| 6,194,902 B1 | 2/2001 | Kuo et al. | |
| 6,271,670 B1 | 8/2001 | Caffey | |
| 6,281,852 B1 | 8/2001 | Amarillas | |
| 6,298,732 B1 | 10/2001 | Burnett | |
| 6,339,333 B1 | 1/2002 | Kuo | |
| 6,472,883 B1 | 10/2002 | Burnett | |
| 6,646,451 B2 | 11/2003 | Lanan | |
| 6,686,746 B2 | 2/2004 | Allan et al. | |
| 6,727,695 B2 | 4/2004 | Krivoi et al. | |
| 6,833,537 B2 | 12/2004 | Risman et al. | |
| 6,889,557 B2 | 5/2005 | Richardson et al. | |
| 6,934,655 B2 | 8/2005 | Jones et al. | |
| 7,196,529 B2 | 3/2007 | Burnett et al. | |
| 2003/0016028 A1 | 1/2003 | Bass | |
| 2004/0199340 A1 | 10/2004 | Kersey et al. | |
| 2005/0007121 A1 | 1/2005 | Burnett et al. | |
| 2005/0072236 A1 | 4/2005 | Heyman et al. | |
| 2006/0145704 A1 * | 7/2006 | Burnett et al. | 324/533 |
| 2008/0191706 A1 * | 8/2008 | Burnett et al. | 324/533 |
| 2010/0116419 A1 * | 5/2010 | Miller et al. | 156/184 |
| 2010/0117622 A1 * | 5/2010 | Miller et al. | 324/71.1 |
| 2010/0171483 A1 * | 7/2010 | Frost et al. | 324/71.1 |

FOREIGN PATENT DOCUMENTS

| | | |
|---|---|---|
| WO | 9628743 | 9/1996 |
| WO | 9732219 | 9/1997 |
| WO | 9855877 | 12/1998 |
| WO | 2004102056 | 11/2004 |
| WO | 2007062221 | 5/2007 |

OTHER PUBLICATIONS

Ishii, "Handbook of Microwave Technology", vol. 1, 1995, 4 pages, Academic Press, San Diego, California.

Caspers et al., "Waveguide Mode Reflectometry for Obstacle Detection in the LHC Beam Pipe Including Signal Attenuation", IEEE, 2003, 3 pages, Geneva, Switzerland.

Kroyer, "A Waveguide High Order Mode Reflectometer for the Large Hadron Collider Beam-pipe", CERN-AB-2003-085 RF, Sep. 2003, 76 pages, Geneva, Switzerland.

Caspers, "Coupler Structures for the LHC Beam Pipe Waveguide Mode Reflectometer", LHC Project Report 764 presented at EPAC, Jul. 2004, 4 pages, Geneva, Switzerland.

Kroyer, "Coupler Structures for the LHC Beam Pipe Waveguide Mode Reflectometer", LHC Project Report 764, presented at EPAC, Jul. 2004, 4 pages, Geneva, Switzerland.

Kroyer, "Application of Waveguide Mode Diagnostics for Remote Sensing in Accelerator Beam Pipes", CERN, Dissertation, Aug. 2005, 135 pages.

Kroyer et al., "Reflectometer Application for the LHC Installation", LTC, Jun. 2006, 14 pages.

Kroyer et al., "Operational Experience with the LHC Waveguide Mode Reflectometer", LHC Project Report 907 presented at EPAC, Jun. 2006, 4 pages, Geneva, Switzerland.

American Gas Association, "Operations Conference & Biennial Exhibition 2007", Apr. 2007, 6 pages, Curran Associates, New York.

Kroyer et al., "The LHC Beam Pipe Waveguide Mode Reflectometer", IEEE, 2007, 3 pages, Geneva, Switzerland.

* cited by examiner

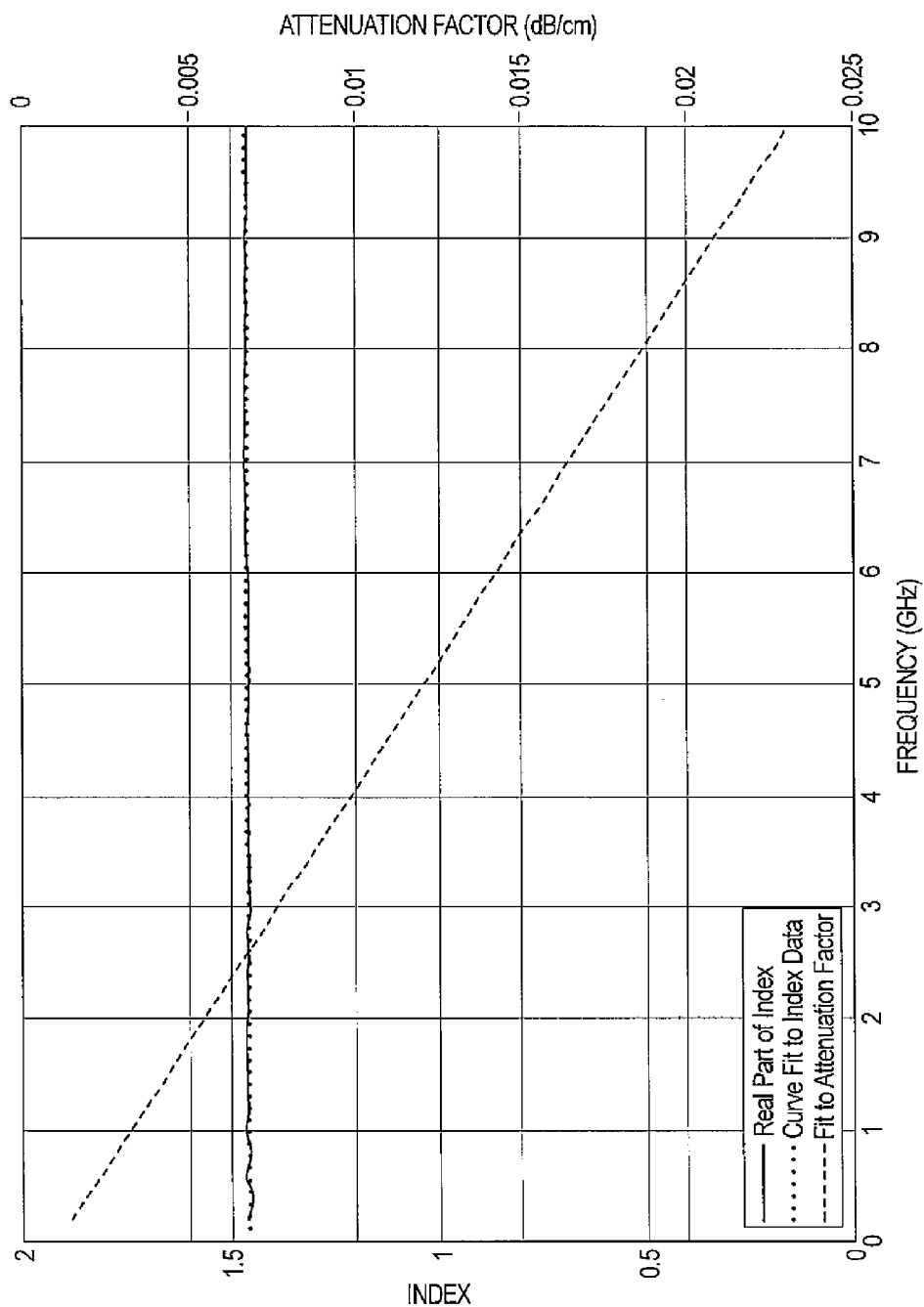
FIG. 2  INDEX OF REFRACTION AND ATTENUATION FACTOR VERSUS FREQUENCY FOR THE DIELECTRIC WAX FILL MATERIAL

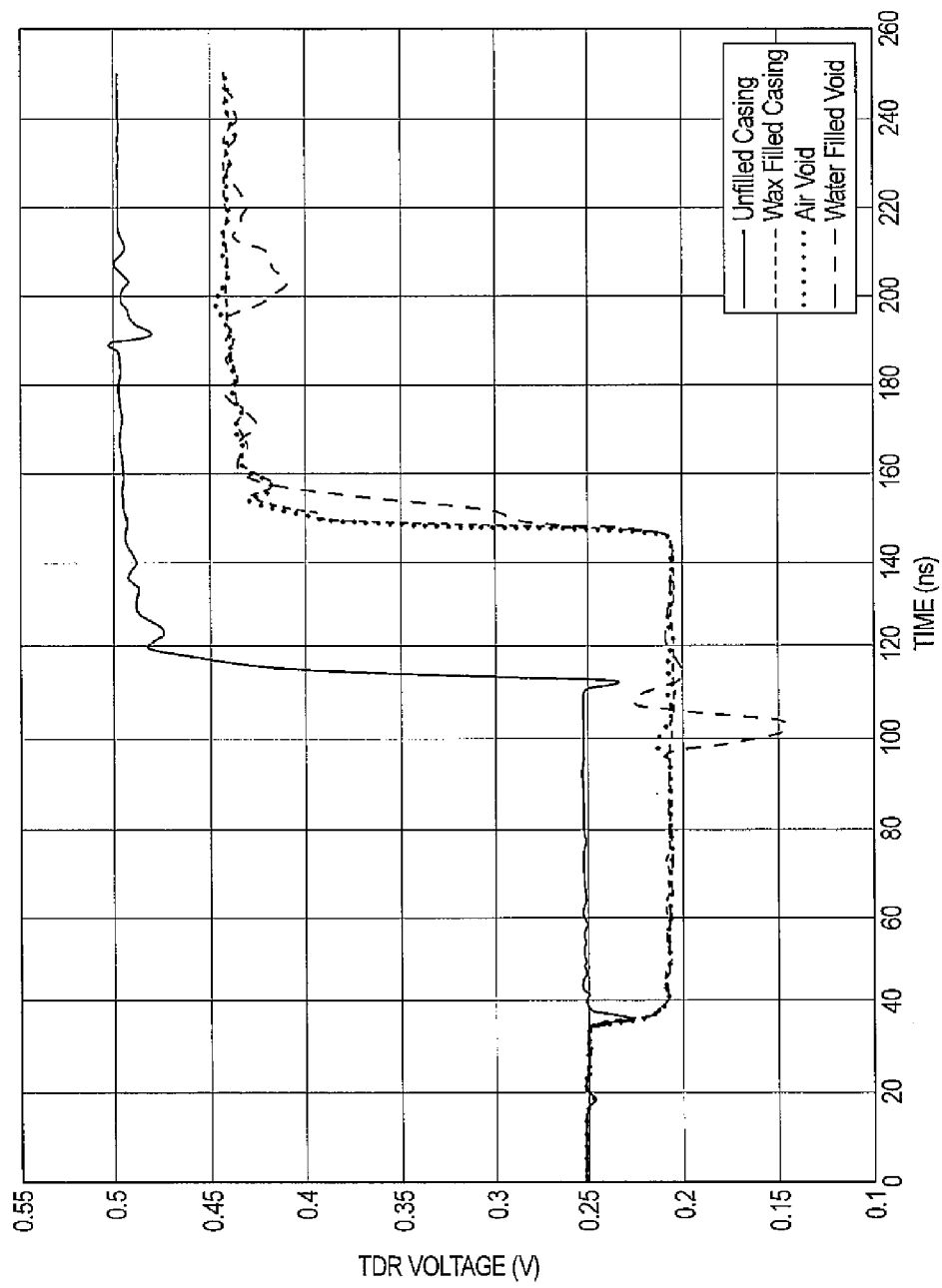
FIG. 3 TDR WAVEFORMS FOR AN UNFILLED CASING, COMPLETELY WAX FILLED CASING, AND FOR AN AIR VOID AND WATER FILLED VOID

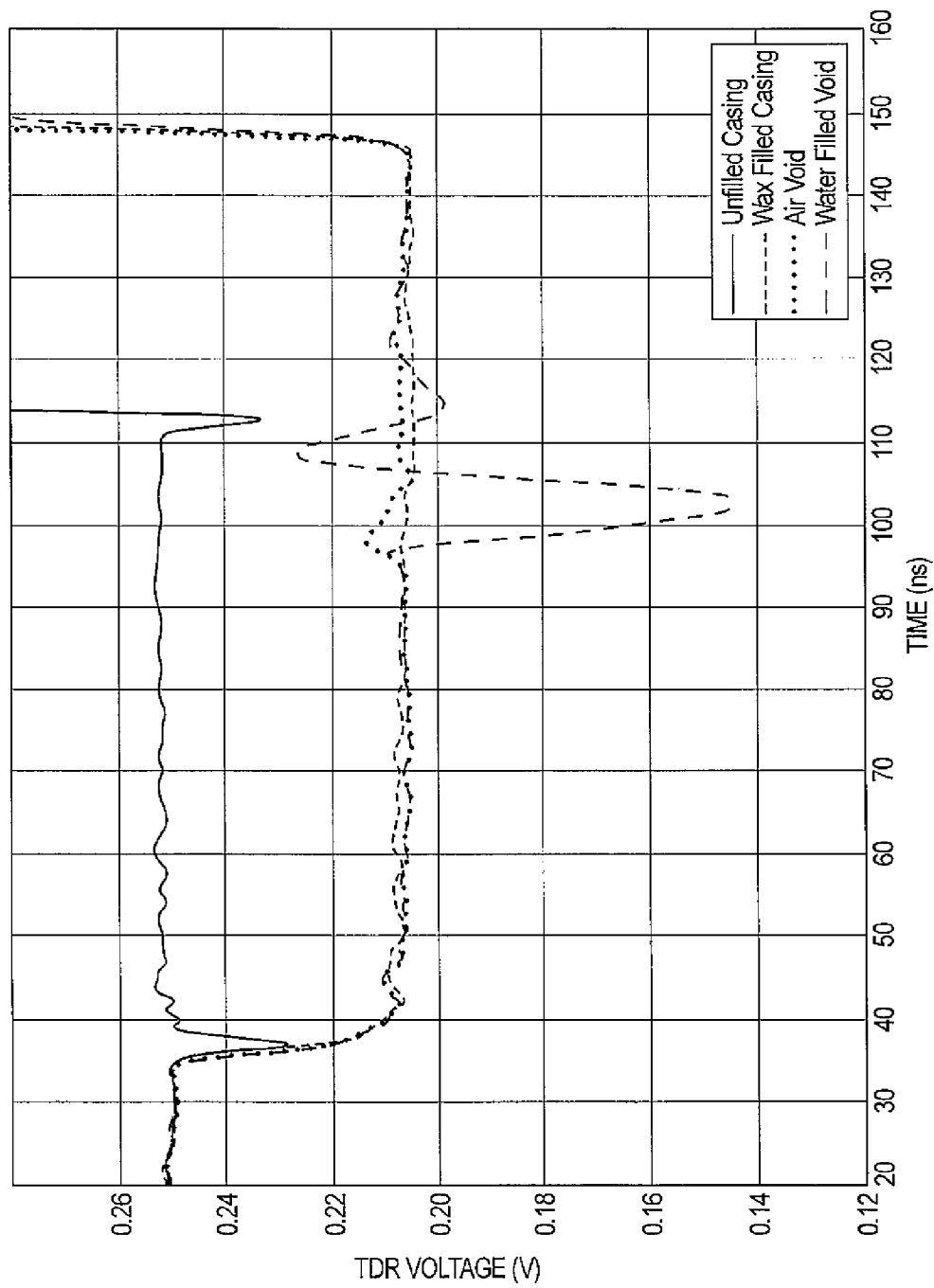
FIG. 4  EXPANDED VIEW OF FIGURE 3.

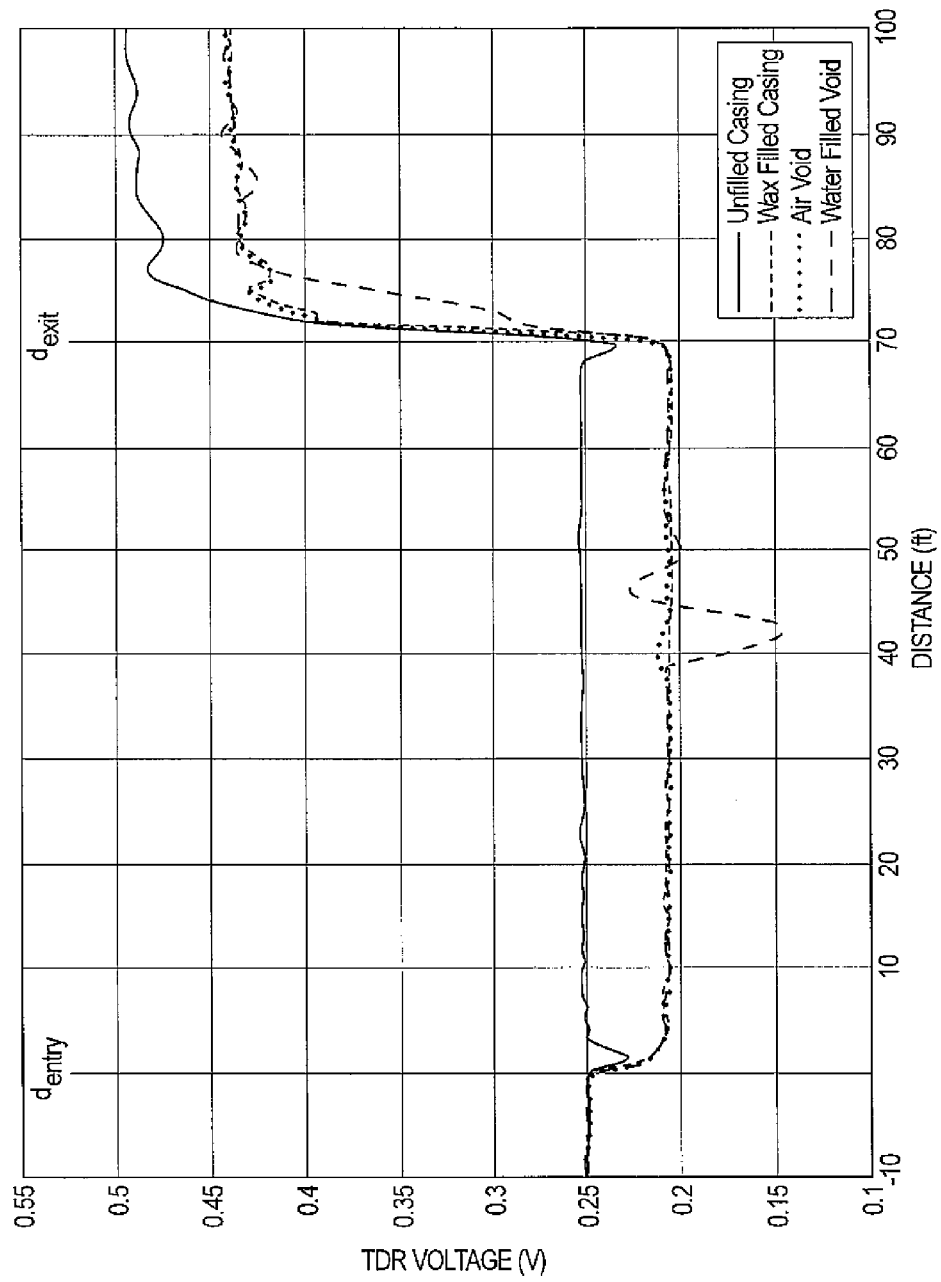
FIG. 5 WAVEFORMS FROM FIGURE 3 PLOTTED ON THE SAME DISTANCE SCALE

MONITORING DIELECTRIC FILL IN A CASED PIPELINE

RELATED APPLICATIONS

This application, U.S. patent application Ser. No. 13/904,998 filed May 29, 2013, is a continuation of U.S. patent application Ser. No. 12/728,143 filed Mar. 19, 2010, now abandoned.

U.S. patent application Ser. No. 12/728,143 claims benefit of U.S. Provisional Application Ser. No. 61/161,714 filed Mar. 19, 2009.

The contents of all related applications listed above are incorporated herein by reference.

TECHNICAL FIELD

The present invention relates to the detection of unfavorable conditions in dielectric fill material surrounding a cased elongate conductive member such as a pipeline and, in particular, to systems and methods for detecting and monitoring for anomalies on the surface and within the annulus of a cased pipeline before, during, and after filling of the casing with dielectric material.

BACKGROUND

A cased pipeline structure typically comprises an internal carrier pipe structure and an external casing pipe structure defining an annulus or annular space that may be filled with dielectric fill material. The carrier pipe structure is typically sized and dimensioned to form a conduit for transporting fluids such as liquids and gases. The casing pipe structure and dielectric fill material are primarily used to protect the carrier pipe structure and/or to contain leaks in the carrier pipe structure.

Anomalies such as differences in materials within the annular space and objects in the annular space of the cased pipeline structure can be introduced during the filling of the annular space or after the cased pipeline structure has been in use. Such anomalies can interfere with proper operation of the cased pipe structure if not removed and/or repaired. The detection of such anomalies can be difficult because access to the annular space and/or access to the cased pipeline structure itself may be difficult, inconvenient, and/or expensive.

In the pipeline industry, the term "crossing" is typically used to refer to the intersection of a cased pipeline structure and another structure such as a road, waterway, other pipeline, or the like. For example, access to the cased pipeline structure at a road crossing requires removal of the road and excavation of the cased pipeline structure, which is typically difficult, inconvenient, and expensive.

The need exists for improved systems and methods for detecting anomalies in cased pipeline structures and in particular to such detection systems and methods that detect anomalies in the annular space defined by such cased pipeline structures, especially at crossings.

RELATED ART

The Applicants are aware of an analysis technique commonly referred to as Time Domain Reflectometry (TDR). TDR is a long range measurement technique that can be used to determine the characteristics of a waveguide structure or transmission line over several hundred feet by observing transmitted and reflected waveforms. This method is similar to RADAR in the way that it works. TDR has been utilized for decades by the telephone, data communications, and cable television industries to detect faults in signal lines.

SUMMARY

The present invention may be embodied as an inspection system comprising a cased pipeline structure, a pulse generator system, a data acquisition system, and a processing system. The cased pipeline structure comprises a casing pipe structure, a carrier pipe structure arranged within the casing pipe structure to define an annular space, and fill material arranged within the annular space. The pulse generator system is configured to apply an electromagnetic signal to the cased pipeline structure. The data acquisition system is configured to detect electromagnetic signals propagating along the cased pipeline structure. The processing system analyzes electromagnetic signals detected by the data acquisition system for signal characteristics indicative of an anomaly in the cased pipeline structure.

The present invention may also be embodied as a method of inspecting a cased pipeline structure having dielectric fill material arranged between a casing pipe structure and a carrier pipe structure, comprising the following steps. An electromagnetic signal is applied to the casing pipe structure and the carrier pipe structure of the cased pipeline structure. At least one probe is arranged within an annular spaced defined between the casing pipe structure and the carrier pipe structure to detect electromagnetic signals propagating along the cased pipeline structure. Electromagnetic signals detected by the at least one probe are analyzed for signal characteristics indicative of an anomaly in the cased pipeline structure.

The present invention may further be embodied as an inspection system for inspecting a cased pipeline structure comprising a casing pipe structure, a carrier pipe structure arranged within the casing pipe structure to define an annular space, and fill material arranged within the annular space. In this example, the inspection system comprises a pulse generator system a data acquisition system, and a processing system. The pulse generator system is configured to apply an electromagnetic signal to the cased pipeline structure. The data acquisition system, which is configured to detect electromagnetic signals propagating along the cased pipeline structure, comprises a data recorder, a first probe, and a second probe. The first probe is arranged in the annular space to detect an electrical component of the electromagnetic signals propagating along the cased pipeline structure. The second probe is arranged in the annular space to detect a magnetic component of the electromagnetic signals propagating along the cased pipeline structure. The processing system analyzes electromagnetic signals detected by the data acquisition system for signal characteristics indicative of an anomaly in the cased pipeline structure.

BRIEF DESCRIPTION OF THE DRAWINGS

FIG. 2 depicts the index of refraction and attenuation factor versus frequency for the dielectric wax fill material;

FIG. 3 depicts TDR waveforms for an unfilled casing, completely wax filled casing, and for an air void and water filled void;

FIG. 4 is an expanded view of FIG. 3;

FIG. 5 depicts waveforms from FIG. 3 plotted on the same distance scale; and

DETAILED DESCRIPTION

Figure 1A:
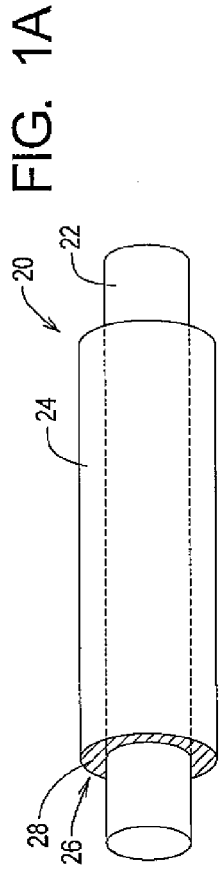
FIG. 1A is a somewhat schematic perspective view of an example cased pipeline structure of the type that may be inspected using the systems and methods of the present invention.
Figure 1B:
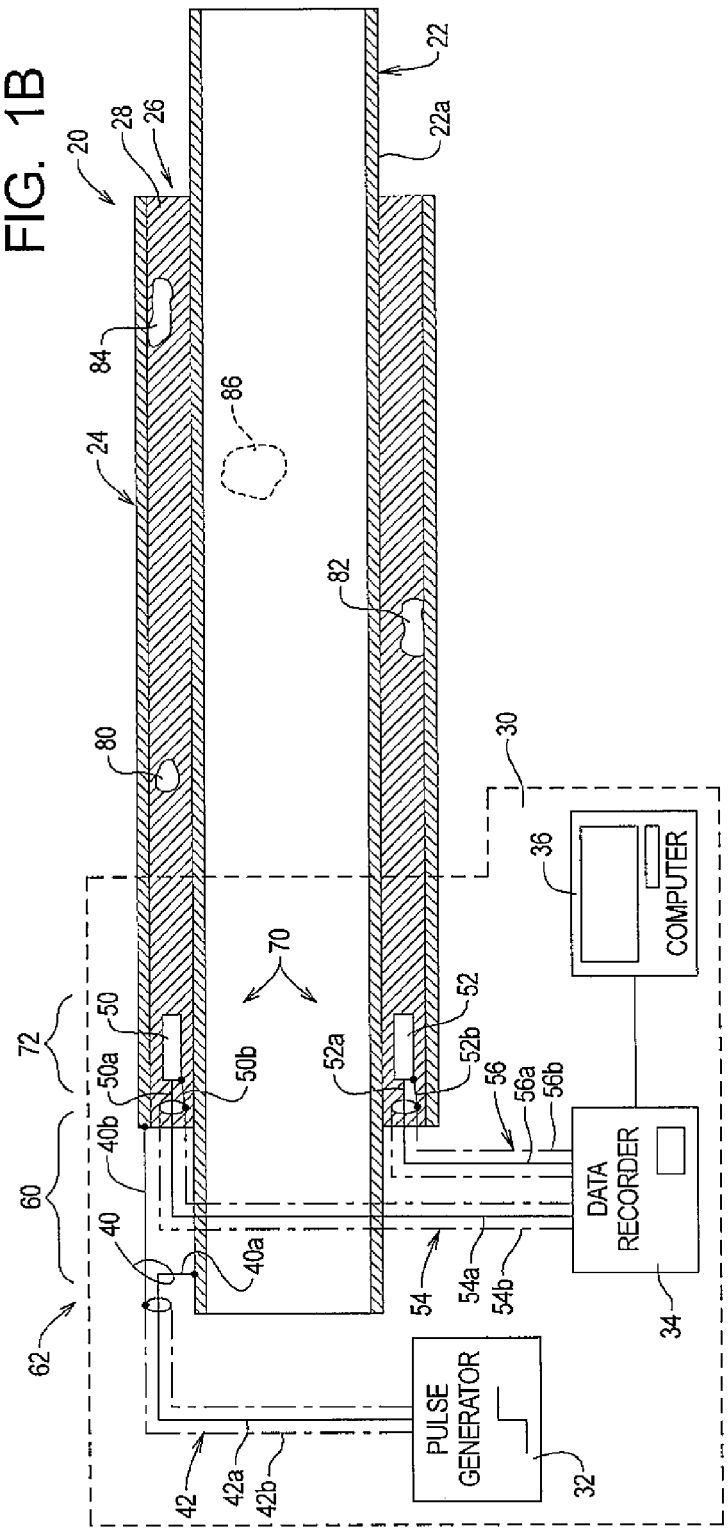
FIG. 1B is a somewhat schematic, section view of the example cased pipeline structure of FIG. 1A and also depicts an example measurement system that may be used to perform dielectric monitoring of the example cased pipeline structure of FIG. 1A.

Shown in FIGS. 1A and 1B is a cased pipeline structure 20 comprising a carrier pipe structure 22 and a casing pipe structure 24 defining an annulus or annular space 26 that may be filled with dielectric fill material 28. The present invention may be embodied as a method and apparatus used to facilitate the application of the fill material 28 and/or to monitor the status of the fill material 28 before, during, and after the cased pipeline structure 20 is filled with the dielectric fill material 28.

When implementing the principles of the present invention, the cased pipeline structure 20 is treated as a coaxial waveguide, and an example method of the present invention utilizes electromagnetic waves to perform time domain reflectometry (TDR) to detect differences from the nominal conditions in the annular space between conducting surfaces of the casing pipe structure 24 and the carrier pipe structure 22. In particular, anomalies such as differences in materials and objects in the annular space 26 of the cased pipeline structure 20 cause reflections which can be measured and related to the physical parameters of the anomaly, and a particular location of the anomaly can be identified.

As a method, the present invention may also be used to detect features and conditions inside the annular space 26 of a cased pipe structure 20 before, during, and after the annular space is filled with a dielectric material. The principles of the present invention may also be implemented as a process for monitoring of a cased pipe structure as the annular space of the cased pipe structure 22 is filled with a flowable dielectric material 28.

The systems and methods of the invention can be used to obtain information about the condition of the annulus 26 that is otherwise unknown because the pipe 22 and casing 24 are buried or very long or conditions otherwise prevent visual inspection. In the context of filling the annulus 26 with dielectric material 28, the present invention may be used to facilitate the fill process by determining the volume of fill material necessary, identifying unknown materials that may block the fill, determining the quantity of fill at discrete locations along the length, identifying locations of voids, and, after the fill process is complete, allowing for monitoring of the annulus 26 for changes resulting from environmental conditions such as water incursion or corrosion growth.

FIG. 1B illustrates that the present invention may be embodied as an example inspection technology or system 30. The example inspection system 30 can be used to facilitate the application of dielectric fill to a cased pipeline and/or to monitor a cased pipeline before, during, and after the application of the dielectric fill material 28 to the annulus 26. Generally speaking, the example inspection system 30 utilizes electromagnetic waves to perform time domain reflectometry (TDR) on the cased pipeline structure 20 to detect differences from the nominal conditions in the annular space between conducting surfaces of the casing pipe structure 24 and the carrier pipe structure 22. The example inspection system 30 can also be used to evaluate pre-fill conditions, aid in the calculation of the volume of dielectric fill material necessary to fill the casing, monitor during the application of dielectric fill material in real time to detect void formation or other problems, and monitor post fill conditions for loss of dielectric fill material or incursion of unwanted material. Each of these aspects or applications of the present invention will be discussed in more detail below.

The Applicants have recognized that certain pipeline configurations, such as cased pipes and crossings, present themselves as a waveguide structure known as a coaxial transmission line and support the propagation of electromagnetic waves. The Applicants have further recognized that these electromagnetic waves can be guided down the cased pipe structure to reveal information about the region between the electrically conducting surfaces of the carrier pipe structure 22 and its casing pipe structure 24. The example inspection system 30 described herein extends the use of TDR to the field of pipeline inspection to provide an entirely new suite of direct assessment, defect detection, and defect characterization capabilities for pipeline integrity management.

A schematic representation of how TDR would be performed on a cased pipe is shown in FIG. 1B. FIG. 1B illustrates that the example inspection system 30 comprises a pulse generator 32, a data acquisition system or recorder 34, and a digital computer 36. FIG. 1B further illustrates that the example inspection system comprises a contact assembly 40 connected to the pulse generator 32 by a first coaxial cable 42 and first and second probes 50 and 52 connected to the data recorder 34 by second and third coaxial cables 54 and 56, respectively. The example first coaxial cable 42 defines a first center conductor 42a and a first shield conductor 42b. The example second and third coaxial cables 54 and 56 define second and third center conductor 54a and 56a and second and third shield conductors 54b and 56b, respectively.

In the context of simple configuration such as a small diameter pipe, the example inspection system 30 employs the single contact assembly 40 arranged at a single injection point 60. In other configurations, additional contacts may be arranged at additional injection points. The example injection point 60 is arranged at an end portion 62 of the cased pipe pipeline structure 20.

As further shown in FIG. 1B, the example contact assembly 40 makes electrical contact with both the carrier pipe structure 22 and the casing pipe structure 24 at the injection point 60. In particular, the example contact assembly 40 comprises a first lead 40a connected between the first center conductor 42a and the carrier pipe structure 22 and a second lead 40b connected between the first shield conductor 42b and the casing pipe structure 24.

The example first probe 50 is an electric field probe, while the example second probe 52 is a magnetic field probe. In the example simple configuration depicted in FIG. 1B, the example inspection system 30 employs the single electric field probe 50 and a single magnetic probe 52 arranged at a single measurement point 70 within the annular space 26 in the fill material 28 between the pipe structures 22 and 24. In other configurations, more than one electric field probe and/or more than one magnetic field probe may be arranged at additional measurement points. The probes 50 and 52 may be used either simultaneously or sequentially depending upon the particulars of the cased pipeline structure under test and the type or types of anomalies suspected to be present. The Applicant's U.S. Pat. Nos. 7,642,790 and 7,940,061, describe systems and methods for processing signals obtained using electric field and magnetic field probes such as the example first and second probes 50 and 52, and the contents of the '790 and '061 patents are incorporated herein by reference.

The example measurement point 70 is arranged at an intermediate portion 72 of the cased pipe pipeline structure 20. The example intermediate portion 72 is adjacent to the end portion 62 but may be spaced from the end portion 62 depending on the structure of the cased pipeline structure 20.

FIG. 1B further shows that the example probes 50 and 52 are arranged in the annular space 26 between the carrier pipe structure 22 and the casing pipe structure 24 at the measurement point 70. In particular, first and second leads 50a and 50b are connected between the example first probe 50 and a second center conductor 54a and a second shield conductor 54b of the second coaxial cable 54, respectively, while first and second lead leads 52a and 52b are respectively connected between the example second probe 52 and a third center conductor 56a and a third shield conductor 56b of the third coaxial cable 56.

FIG. 1B further illustrates several example anomalies in the example cased pipelines structure 20 that can be detected and located using the example inspection system 30. Depicted at 80 is a first example anomaly in the form of an object that is embedded within the dielectric material 28. Reference character 82 represents a second example anomaly in the form of water incursion into the dielectric material 28. Reference character 84 represents a third example anomaly in the form of an air void within the dielectric material 28. Reference character 86 represents an area of external corrosion on an outer surface 22a of the carrier pipe structure 22.

Given the foregoing general understanding of the example inspection system 30, the details of use of this system 30 will now be described. As an initial part of any test, calibrations are performed to determine the wave velocity in the casing so that distances to anomalies can be determined. With a measured or known casing length, calibration waveforms acquired versus time allow measuring the time of flight and the wave velocity to be calculated. For a casing of unknown length, the wave velocity can be estimated allowing the length of the casing to be calculated.

With known calibration information and measurements of the geometry of the casing structure, the example inspection technology can be used to better calculate the volume of dielectric fill material that will be necessary for a given situation. Casing lengths can be precisely calculated using the example inspection technology data and compared to drawings in order to confirm or dispute existing information.

The Applicants have used a coaxial line diagnostic representing a scale model of a casing to determine the complex permittivity of a sample of dielectric wax commonly used as a casing filler for corrosion protection of the carrier pipe. The diagnostic compares pulses reflected from and transmitted through equivalent lengths of a reference air filled coaxial line and one filled with the dielectric material under test to determine the frequency dependent complex permittivity, i.e. the dielectric constant and attenuation factor versus frequency. The inventors found that the wax sample was a very good dielectric which exhibited a broadband dielectric constant with low attenuation.

Results of the frequency domain analysis are shown in FIG. 2. It is seen that the index of refraction is fairly flat across the entire frequency range and that the attenuation factor is relatively small. At a frequency of 1 GHz, the index of refraction is 1.4626 (i.e. a permittivity or dielectric constant of ~2.14) and the attenuation factor is −0.0033 dB/cm. If the attenuation factor is compared to a commercially available coaxial line with a solid polyethylene (PE) dielectric, such as RG-8A/U, a perspective of the amount of loss can be determined. At a frequency of 1 GHz, RG-8A/U has an attenuation of 9 dB/100 ft. Through calculation, the wax dielectric will have an attenuation of 10.06 dB/100 ft at 1 GHz. This means that the loss and dispersion in the wax are low. As such, the pulses should easily propagate through wax filled casings of typical lengths, i.e. on the order of hundreds of feet.

The permittivity of the wax sample was also estimated by two other methods. One method looks at the difference in the arrival time of pulses transmitted through an air filled line and a wax filled line of the same length. Using this method, the relative permittivity is estimated to be 2.145. Another method measures the capacitance of the wax filled coaxial line and calculates the relative permittivity based on its relationship to the capacitance of the line. Using this method, the relative permittivity at 100 kHz is estimated to be 2.347. The average of all measurements gives a relative permittivity of 2.211.

The Applicants also analyzed data obtained using the example inspection technology for a casing under the following conditions: unfilled, wax filled, wax filled with an air void, and wax filled with water encroachment into a void. To generate these waveforms, the air filled and wax filled coaxial lines were used to determine the permittivity and attenuation factor of the dielectric wax sample. To simulate the air void and water filled void, a small hole was drilled in the outer casing of the test line and a small volume of the wax was removed. The air void is simulated first and then the air void was filled with water.

Plotted in FIG. 3 on the same time scale are waveforms generated by the example inspection technology for the four cases noted above. Data is plotted on the same time scale since the wave velocity factor decreases as the casing is filled with wax. The graphs show what one would expect to see for the clean casing and then after filling it with wax. If the casing is perfectly filled with wax, the impedance drops and the velocity factor decreases. As such, it takes the TDR pulse longer to reach the end of the casing. Based on the properties of the wax and the geometry of the casing, one can calculate ahead of time what one would expect to see for these two situations. A casing uniformly filled with wax will exhibit a relatively flat TDR waveform. Non-uniformities in the wax fill would be evident in the TDR waveform.

FIG. 4 depicts an expanded view of the TDR waveforms shown in FIG. 3 to better illustrate what one would observe from an air void and the same air void filled with water. In this case, the air void is very small, representing removal of wax from ~90 degrees of the circumference over a length of 1.4 percent of the entire length of the casing.

Water filling of the air void gives a much larger effect due to the large permittivity of water. Also note that an air void causes the impedance to increase and a water filled void causes the impedance to decrease. Thus, if an air void was detected and monitored over time, it would be relatively easy to detect incursion of water or other unwanted material. Similarly, with a "good fill" baseline, it would be relatively easy to detect loss of material and/or water incursion by subtracting the baseline data from data taken periodically after the wax fill.

Using the open circuit at the far end of the casing as a calibration marker, as shown in FIG. 5 one can calculate the different velocity factors for the unfilled and filled casings and plot the data generated using the example inspection technology on the same distance scale. The usefulness of the example inspection technology in casing wax fill situations is summarized as follows: The technology can be used to evaluate conditions in the casing prior to and after flushing. It can be used to determine the length of a casing or verify existing measurements in order to more accurately predict the volume of wax necessary for the fill. It can be used to monitor the wax fill in real time to immediately detect problems or void formation. After wax filling, a baseline may be established; the baseline facilitates detection of changes in the cased pipeline structure 20 with reference to the baseline by performing periodic monitoring and subtracting or otherwise referencing the baseline configuration as represented by the baseline data.

The pulse generator 32, data acquisition system 34, and computer 36 all are or may be conventional and will not be described in detail herein beyond what is helpful for a complete understanding of the principles of the present invention. The example pulse generator 32 is capable of applying a step pulse to the cased pipeline structure 20 under test such that the step pulse propagates along the length of the portion of the cased pipeline structure 20. The data acquisition system 34 is any signal detection system capable of detecting and recording fast transient signals propagating along the cased pipeline structure 20 that are detected by the first and/or second probes 50 and 52. For example, these probes 50 and/or 52 may detect the original step pulse generated by the pulse generator 32 and/or any reflected signals resulting from anomalies in or structural features of the cased pipeline structure 20. The computer 36 is, in general, any computational device that is capable of running code written to control data acquisition and process data and may take the form of a standalone computer or a computer or programmable gate array built in to the data acquisition system.

As described above, data is recorded, stored, and analyzed to implement the principles of the present invention. The example computer 36 communicates with the data acquisition system 34 to control collection of data, transfer data to a storage system, and process the raw data into a meaningful result for the operator. Processing of the raw data is performed in order to automate certain data collection and analysis tasks to facilitate the detection, identification, and or location of any anomalies in the cased pipeline structure under test.

For example, the software running on data acquisition system 34 and/or the computer 36 may perform any one or more of the following data storage, processing, and/or analysis operations on data associated with signals generated by the example first probe 50 (e.g., differentiating electric field (D-dot) probe) and example second probe 52 (magnetic field (B-dot) probe):

- combining the data representing signals generated by the example first and second probes to ascertain the directionality of anomalies from a single probing or measurement location;
- subtracting or otherwise taking into account a pre-trigger baseline data from data representing measured signals to account for the effect any DC offsets in the cased pipeline structure under test;
- implementing de-skewing analysis data representing measured signals to account for any differences in the time of arrival of signals at the inputs to the data acquisition system;
- adding of the data representing signals or waveforms obtained from the example first (D-dot) and second (B-dot) probes to form an impulse transmission waveform;
- subtracting the data representing the signal detected by the first probe (B-dot signal) from data representing the signal detected by the second probe (D-dot signal) to form an impulse reflection waveform;
- integrating impulse waveforms to form step waveforms that are related to the step pulse that is injected into the pipe system and return signals that may be reflected back from the cased pipeline structure forming the system under test;
- processing data to enhance the data and aid in characterization of any anomalies detected;
- transforming the impulse time domain waveforms into the frequency domain using a fast Fourier transform (FFT) or other transform (transformation to the frequency domain allows the operator to ascertain the measured impulse response of the system (i.e. the pipeline configuration under test) in the frequency domain, more generally known as the impulse response);
- using the impulse response to determine the response of the system to other inputs;
- performing additional frequency domain processing to filter the data and look at specific frequency bands or components of detected or measured signals associated with anomalies and also to correct the measured data for frequency dependent attenuation;
- calculating a synthetic numerical pulse based on the impulse response of the system under test that may be injected into the cased pipeline structure system under test to reduce or eliminate unwanted reflections from, for example, faulty connectors or cable mismatches; synthetic pulse injection also allows for improved resolution and elimination of ghost anomalies due to reflections re-injected into the system.

Figure 6:
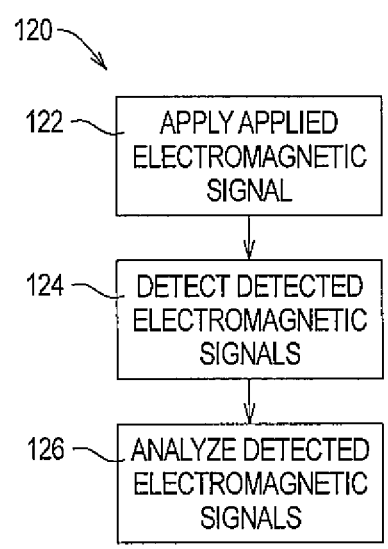
FIG. 6 contains a flow chart depicting a method of inspecting a cased pipeline structure of the present invention.

Referring now to FIG. 6 of the drawing, depicted at 120 therein is an example method embodying the principles of the present invention. In particular, the example method 120 is a method of inspecting a cased pipeline structure such as the example cased pipeline structure 20 having dielectric fill material such as the example fill material 28 arranged between a casing pipe structure such as the casing pipe structure 24 and a carrier pipe structure such as the example carrier pipe structure 22.

As shown in FIG. 6, the example method 120 comprises the step 122 of applying an applied electromagnetic signal to the casing pipe structure and the carrier pipe structure of the cased pipeline structure. At least one probe is arranged at step 124 within an annular space defined between the casing pipe structure and the carrier pipe structure to detect detected electromagnetic signals propagating along the cased pipeline structure. Electromagnetic signals detected by the at least one probe are analyzed at step 126 for signal characteristics indicative of an anomaly in the cased pipeline structure.

In the example inspection system 30, the example pulse generator 32 is configured to apply an applied electromagnetic signal to the cased pipeline structure. The data acquisition system 34 is configured to detect electromagnetic signals propagating along the cased pipeline structure. The processing system 36 analyzes electromagnetic signals detected by the data acquisition system 34 for signal characteristics indicative of an anomaly in the cased pipeline structure 20.

The present invention thus takes the form of systems and methods for inspecting cased pipeline structures that are sufficiently flexible to accommodate cased pipeline structures of various diameters, lengths, structures, and configurations. Based on the description of the example systems and methods described above, one of ordinary skill in the art will understand that the operator will need to vary the basic inspection system and use appropriate data processing and analysis techniques based on the characteristics of particular cased pipeline structure under test.

The scope of the present invention should thus be determined based on the claims appended hereto and not the foregoing detailed description of one example of an implementation of the present invention.

What is claimed is:

1. An inspection system comprising:
    a cased pipeline structure comprising
        a casing pipe structure,
        a carrier pipe structure arranged within the casing pipe structure to define an annular space, and
        fill material arranged within the annular space;
    a pulse generator system configured to apply an applied electromagnetic signal to the cased pipeline structure such that electromagnetic characteristics of the fill material alter the electromagnetic signal as the electromagnetic signal propagates along the cased pipeline structure;
    a data acquisition system configured to detect detected electromagnetic signals propagating along the cased pipeline structure; and
    a processing system for analyzing detected electromagnetic signals detected by the data acquisition system for signal characteristics associated with the electromagnetic characteristics of the fill material that are indicative of an anomaly in the fill material arranged within the annular space of the cased pipeline structure; wherein
    the pulse generator system applies the electromagnetic signal, the data acquisition system detects the detected electromagnetic signals, and the processing system analyzes the detected electromagnetic signals in real time while the fill material is being arranged between the casing pipe structure and the carrier pipe structure.

2. An inspection system as recited in claim 1, in which the pulse generator system comprises:
    a pulse generator; and
    a contact assembly operatively connected to the casing pipe structure and the carrier pipe structure.

3. An inspection system as recited in claim 1, in which the data acquisition system comprises:
    a data recorder; and
    at least one probe arranged in the annular space to detect the detected electromagnetic signals propagating along the cased pipeline structure.

4. An inspection system as recited in claim 3, in which the at least one probe detects an electrical component of the detected electromagnetic signals propagating along the cased pipeline structure.

5. An inspection system as recited in claim 3, in which the at least one probe detects a magnetic component of the detected electromagnetic signals propagating along the cased pipeline structure.

6. An inspection system as recited in claim 1, in which the data acquisition system comprises:
    a data recorder; and
    a first probe arranged in the annular space to detect an electrical component of the detected electromagnetic signals propagating along the cased pipeline structure; and
    a second probe arranged in the annular space to detect a magnetic component of the detected electromagnetic signals propagating along the cased pipeline structure.

7. An inspection system as recited in claim 1, in which the processing system comprises software for:
    determining baseline data representative of the cased pipeline structure without anomalies; and
    comparing data corresponding to the detected electromagnetic signals with the baseline data.

8. An inspection system as recited in claim 1, in which the processing system comprises software for transforming the detected electromagnetic signals from the time domain into the frequency domain.

9. A method of inspecting a cased pipeline structure having dielectric fill material arranged between a casing pipe structure and a carrier pipe structure, comprising the steps of:
    applying an applied electromagnetic signal to the casing pipe structure and the carrier pipe structure of the cased pipeline structure such that electromagnetic characteristics of the dielectric fill material alter the electromagnetic signal as the electromagnetic signal propagates along the cased pipeline structure;
    arranging at least one probe within an annular space defined between the casing pipe structure and the carrier pipe structure to detect detected electromagnetic signals propagating along the cased pipeline structure; and
    analyzing the detected electromagnetic signals detected by the at least one probe for signal characteristics associated with the electromagnetic characteristics of the dielectric fill material that are indicative of an anomaly in the dielectric fill material arranged within the annular space of the cased pipeline structure; wherein
    the steps of applying the electromagnetic signal, arranging the at least one probe, and analyzing the detected electromagnetic signals are performed in real time as the fill material is being arranged between the casing pipe structure and the carrier pipe structure.

10. A method as recited in claim 9, in which the step of applying the applied electromagnetic signal to the casing pipe structure comprises the steps of:
    providing a pulse generator;
    operatively connecting the pulse generator to the casing pipe structure and the carrier pipe structure; and
    operating the pulse generator.

11. A method as recited in claim 9, in which the step of arranging at least one probe to detect the detected electromagnetic signals propagating along the cased pipeline structure comprises the steps of:
    providing a data recorder; and
    operatively connecting the at least one probe to the data recorder.

12. A method as recited in claim 9, in which the step of arranging at least one probe to detect the detected electromagnetic signals propagating along the cased pipeline structure comprises the steps of:
    providing a D-dot probe; and
    operatively connecting the D-dot probe to a data recorder.

13. A method as recited in claim 9, in which the step of arranging at least one probe to detect the detected electromagnetic signals propagating along the cased pipeline structure comprises the steps of:
    providing a B-dot probe; and
    operatively connecting the B-dot probe to a data recorder.

14. A method as recited in claim 9, in which the step of arranging at least one probe to detect the detected electromagnetic signals propagating along the cased pipeline structure comprises the steps of:
    providing a data recorder; and
    arranging a first probe in the annular space to detect an electrical component of the detected electromagnetic signals propagating along the cased pipeline structure; and
    arranging a second probe in the annular space to detect a magnetic component of the detected electromagnetic signals propagating along the cased pipeline structure.

15. A method as recited in claim 9, in which the step of analyzing the detected electromagnetic signals propagating along the cased pipeline structure comprises the steps of:
    determining baseline data representative of the cased pipeline structure without anomalies; and comparing data corresponding to the detected electromagnetic signals with the baseline data.

16. A method as recited in claim 9, in which the step of analyzing the detected electromagnetic signals propagating along the cased pipeline structure comprises the step of transforming the detected electromagnetic signals from the time domain into the frequency domain.

17. An inspection system for inspecting a cased pipeline structure comprising a casing pipe structure, a carrier pipe structure arranged within the casing pipe structure to define an annular space, and fill material arranged within the annular space, the inspection system comprising:
   a pulse generator system configured to apply an applied electromagnetic signal to the cased pipeline structure such that electromagnetic characteristics of the fill material alter the electromagnetic signal as the electromagnetic signal propagates along the cased pipeline structure;
   a data acquisition system configured to detect detected electromagnetic signals propagating along the cased pipeline structure, the data acquisition system comprising
      a data recorder,
      a first probe arranged in the annular space to detect an electrical component of the detected electromagnetic signals propagating along the cased pipeline structure, and
      a second probe arranged in the annular space to detect a magnetic component of the detected electromagnetic signals propagating along the cased pipeline structure; and
   a processing system for analyzing the detected electromagnetic signals detected by the data acquisition system for signal characteristics associated with the electromagnetic characteristics of the fill material that are indicative of an anomaly in the fill material arranged within the annular space of the cased pipeline structure; wherein
   the pulse generator system applies the electromagnetic signal, the data acquisition system detects the detected electromagnetic signals, and the processing system analyzes the detected electromagnetic signals in real time while the fill material is being arranged between the casing pipe structure and the carrier pipe structure.

18. An inspection system as recited in claim 17, in which the pulse generator system comprises:
   a pulse generator; and
   a contact assembly operatively connected to the casing pipe structure and the carrier pipe structure.

19. An inspection system as recited in claim 17, in which the processing system comprises software for:
   determining baseline data representative of the cased pipeline structure without anomalies; and
   comparing data corresponding to the detected electromagnetic signals with the baseline data.

20. An inspection system as recited in claim 17, in which the processing system comprises software for transforming the detected electromagnetic signals from the time domain into the frequency domain.

* * * * *